United States Patent [19]

Gelbard

[11] Patent Number: 5,676,703
[45] Date of Patent: Oct. 14, 1997

[54] SPINAL STABILIZATION IMPLANT SYSTEM

[76] Inventor: Steven D. Gelbard, 8130 Royal Palm Blvd., Ste 200, Coral Springs, Fla. 33065

[21] Appl. No.: 692,850

[22] Filed: Jul. 24, 1996

Related U.S. Application Data

[62] Division of Ser. No. 241,356, May 11, 1994, abandoned.

[51] Int. Cl.$^6$ .................................................. A61F 2/44
[52] U.S. Cl. .................. 623/17; 606/61; 411/383; 411/389
[58] Field of Search .................. 606/61, 62, 72, 606/73; 623/17; 411/383, 384, 389, 400

[56] References Cited

U.S. PATENT DOCUMENTS

| | | | |
|---|---|---|---|
| 4,742,663 | 5/1988 | Demers | 411/389 |
| 5,387,212 | 2/1995 | Yuan | 606/61 |
| 5,474,551 | 12/1995 | Finn | 606/61 |
| 5,498,263 | 3/1996 | Di Nello | 606/61 |
| 5,505,731 | 4/1996 | Tornier | 606/61 |
| 5,545,166 | 8/1996 | Howland | 411/389 |
| 5,562,661 | 10/1996 | Yoshimi | 606/61 |

Primary Examiner—Michael J. Milano
Attorney, Agent, or Firm—McHale & Slavin, P.A.

[57] ABSTRACT

A surgical implant system for the stabilization of a human spine by fixation of the vertebra utilizing a stabilization cross-link spinal implant system. The system utilizes self-tapping screws having bifurcated protruding members to support an alignment rod, the protruding members available for placement of a fixed or variable traverse cross-link member that couples to the protruding members by use of threaded nuts corresponding to the threaded portion of the outer surface of the protruding members. The externally threaded coupling method can also be use for pedicle, caudal, cranial, thoracic and the like hooks. Also shown is a two plate system for anterior cervical spine fixation.

7 Claims, 7 Drawing Sheets

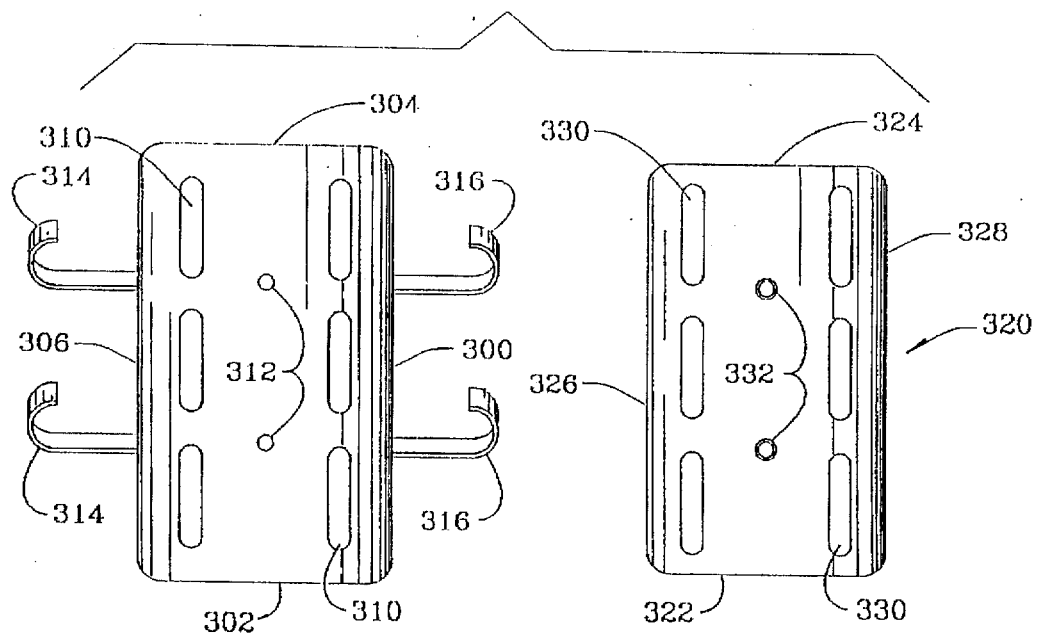
FIG. 13
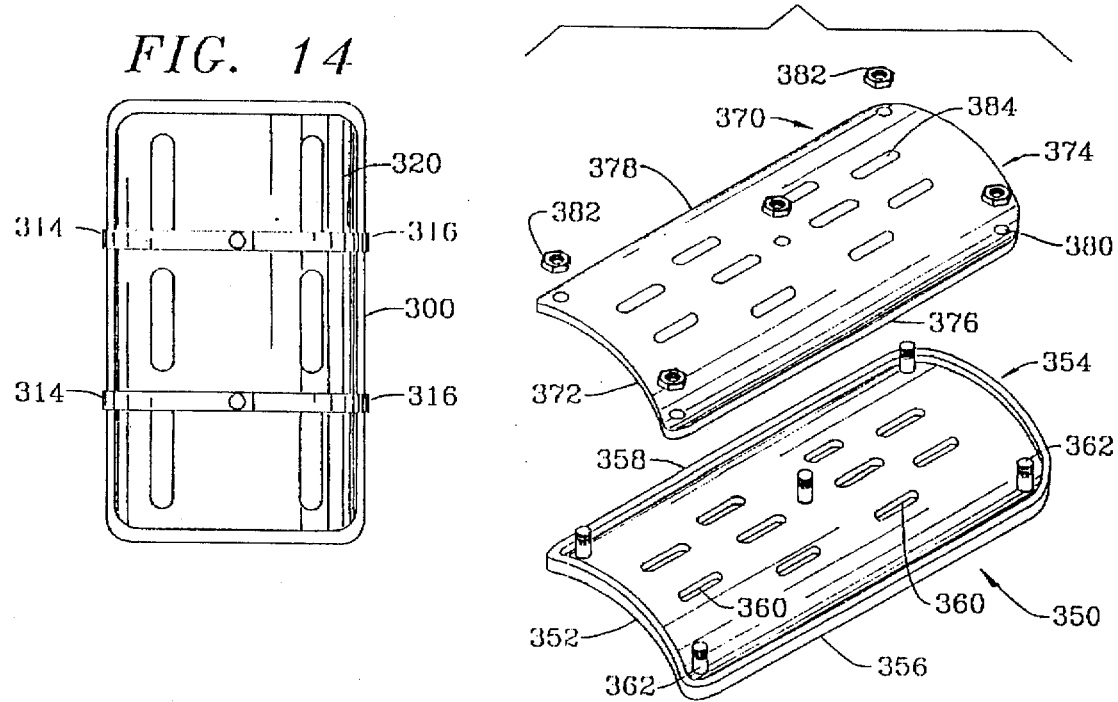
FIG. 14
FIG. 15

SPINAL STABILIZATION IMPLANT SYSTEM

This is a divisional of application Ser. No. 08/241,356, filed on May 11, 1994, now abandoned.

BACKGROUND OF THE INVENTION

1. Field of the Invention

This invention relates generally to spinal implants and, in particular, to a spinal implant having a novel top-loading bolt attachment for support and alignment rods with cross links and ancillary components for stabilization of the vertebrae as well as a two plate system for cervical spine fixation.

2. Background of the Invention

Surgical implants are well known in the art for treatment of curvatures of the spine including anterior, trauma, deformity, and/or degenerative spinal conditions. The purpose of the implant is to reinforce the spine by use of strategically placed attachment screws capable of supporting alignment support rods placed bilateral along the vertebrae as well as cross-link members that bridge the sagittal of the spine.

The problem which this invention addresses is the method of fastening the spinal implants during surgery. Conventionally, the placement of an attachment screw provides the functional base for the support rod, cross-link, caudal facing hooks, cranial facing hook and the like components that form a spinal implant system. The conventional method of fastening utilizing a goal post mounting screw from which a bolt and nut is coupled perpendicular thereto for mounting to the component. This side attachment frequently requires the movement of muscle and other tissue during operation which increases the difficulty of the operation, is a time consuming effort, and can be a major trauma to a person.

In addition, the use of the prior art devices required prethought to where the cross-links are to be placed. Once the base screws are installed, they cannot be moved and if the screws are placed incorrectly, the cross-link will not fit.

U.S. Pat. No. 5,084,048, issued to Jacob et al., entitled "Implant for Vertebrae With Spinal Stabilizer" discloses a vertebrae implant having a stabilizing element which is articulated to accommodate a pair of bone screws wherein each bone screw includes a clamp disposed between a shoulder in a spherical surface which is all coupled together by the use of a clamping nut directly on the end of the bone screw. The device allows for support of an alignment rod along the side of the bone screw, but fails to provide any type of cross link or ancillary component attachment devices.

U.S. Pat. No. 4,041,939, issued to Hall, entitled "Surgical Implant Spinal Screw" discloses a spinal implant utilizing a screw having a centrally disposed aperture for placement of a metal cable therethrough with a nylon insert that will permanently secure the cable in a fixed position once attached. The device is best used in an operation for the correction of scoliosis.

Another problem with prior art is the use of anterior cervical plates. The prior art employs a single plate that is attached by the use of small bone attachment screws. After installation, the screws have a tendency of working their way out of the bone resulting in the loosening of the cervical plate causing the patient pain and typically resulting in further surgery to correct the problem.

Therefore there exists a need to correct the aforementioned problems by use of a top loading spinal implant system and associated cervical plate attachment cover.

SUMMARY OF THE INVENTION

The instant invention is a surgical implant system for the stabilization of the human spine by fixation of the vertebra. The system is based upon screws, nuts, rods,. hooks, cross-members and variations thereof. The preferred embodiment employs a metal screw for placement in the sacrum or pedicle defined by a coarse self-tapping thread and a U-shaped saddle for placement of conventional alignment rods. Unique to this invention is that the screw is threaded on the outer surface of the saddle allowing the alignment rod to be securely fastened into the saddle by placement of the rod therein and the fastening of a nut to the top of saddle. Further unique to this invention is the use of an elongated sagittal traverse support member that can accommodate the saddle protrusion either in a fixed position or by use of a rotatable insert that allows the cross member to be tightly fastened to the saddle in a variable alignment. The top-loading attachment is further applicable to caudal, cranial, and the like hook components.

An anterior cervical plate is set forth using a second plate to permanently lock the cervical plate in position. The second plate does not rely upon the bone to support the plate thus providing a means to prevent any bone attachment screws from loosening or otherwise backing out of the bone.

Accordingly, an objective of the instant invention is to provide thoracic lumbar stabilization by use of linking conventional support alignment rods placed bilaterally along the vertebrae with the top-loading sacral and pedicle screws of the instant invention.

Still another objective is to lessen the need for ancillary tissue movement during surgery by use of a top mounted attachment means for ancillary components and provide a variable attachment system to provide the surgeon with fixation components that will accommodate a variety of circumstances.

Yet another objective of the instant invention is to provide a cross-link member that is operatively associated with the attachment screws by means of a top mounted link that is receptive to the protruding members of the screws or separate cross link attachments.

Yet still another objective of the instant invention is to provide a variable attachment means for two member and four member attachment screws by the use of rotatable attachment slots within the cross-link members.

Still another objective of the instant invention is to simplify the means for attaching caudal, thoracic, cranial and the like hooks by use of a top loading fastening nut that is threaded directly onto the hook body.

Still another objective of the instant invention is to provide an improved sacral and pedicle pinion post screw that allows angular bridging by use of an indexing right angled base having the means for coupling to another right angled base.

Yet still another objective is to disclose an improved anterior dervical plate having a second plate that couples to the cervical mounted plate effectively locking the cervical mounted plate in position by preventing the retraction of the mounting screws, while allowing the mounting screws to be put in at various angles and positions.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the instant invention and illustrate various objects and features thereof.

BRIEF DESCRIPTION OF THE DRAWINGS

FIG. 13 is a top view of an anterior cervical plate using a strap embodiment;

FIG. 14 is a perspective view of the anterior cervical plates with the strap embodiment in an attached position;

FIG. 15 is a perspective view of another two plate anterior cervical plate with the strap embodiment in an attached position;

DETAILED DESCRIPTION OF THE PREFERRED EMBODIMENT

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Figure 1:
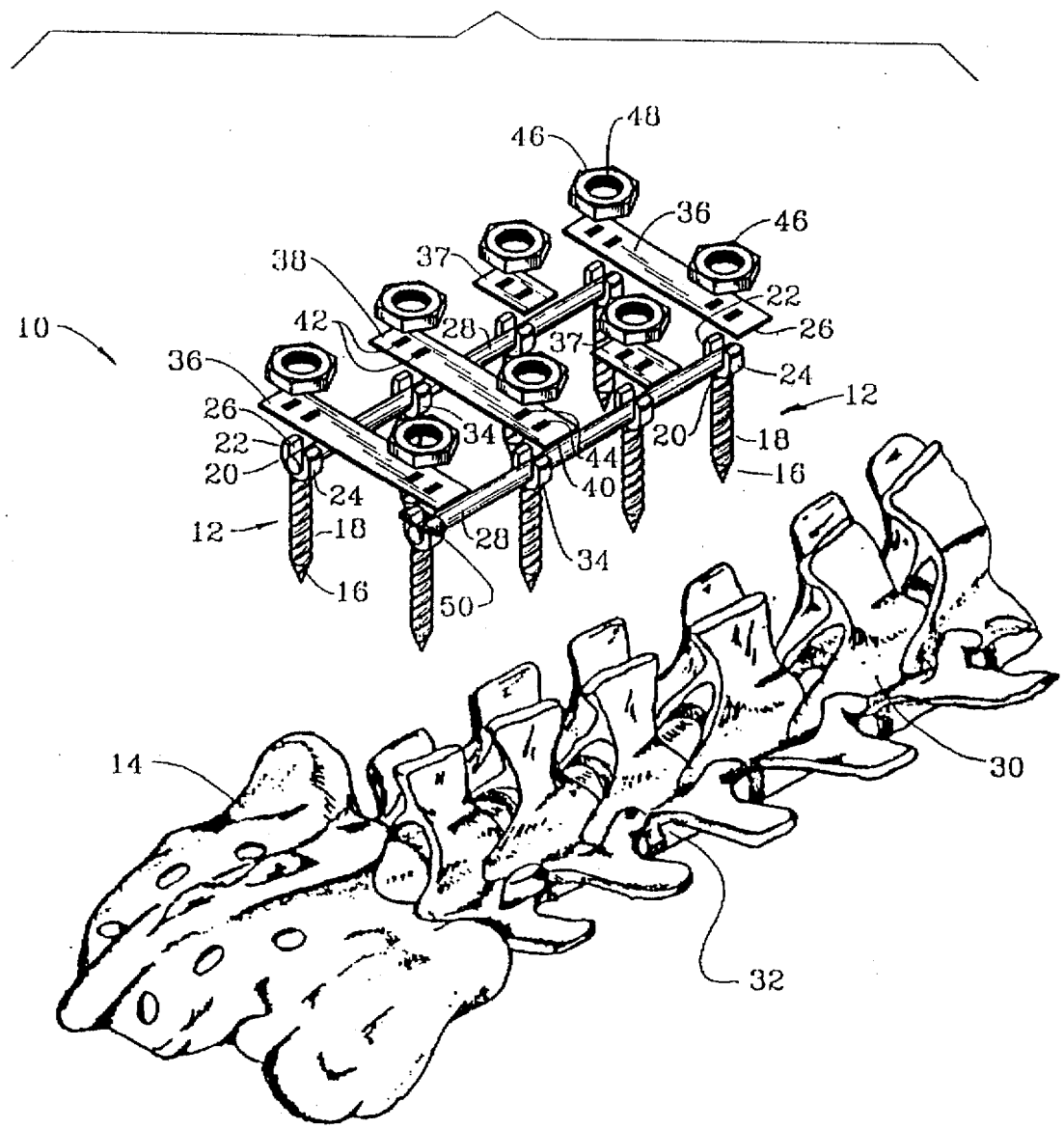
FIG. 1 is an exploded perspective view of the preferred embodiment of the instant invention.

Now referring to FIG. 1, the surgical implant system of the instant invention is generally shown as numerated 10 for use in the stabilization of a human spine by fixation of vertebra. The construction materials consist of stainless steel, titanium, or the like high quality material. The base of the system employs a spinal screw 12 shown diverging in the sacrum 14. The sacral screw 12 characterized by a first end 16 having a relatively coarse self-tapping thread 18 over a major portion of its length. A second end 20 having a first 22 and second 24 spaced apart protruding member extending obliquely from the screw defining an inner surface saddle 26 having an inner diameter corresponding to the outer diameter of a conventional support alignment rod 28. The screw can be made of various lengths and diameters, the size dependant upon the location for placement, the amount of support or reconstruction required, and the actual size of the individual's bone structure. The outer surface of the second end 20 of the screw 12 includes a plurality of grooves placed therein to form a partial thread 34. The threads 34 can be cast or placed on the surface by means of a conventional thread shaping die. The saddle 26 receptive to an alignment support rod 28 placed along the length of the vertebra 30 of the spine 32 to provide longitudinal support.

A rectangular shaped rigid plate 36 can then be used to connect two sagittal placed screws 12. The plate 36 is defined as an elongated sagittal traverse support member having first 38 and second end 40 and two edges and upper and lower reversible surface. At the first end 36 is placed an opening 42 operatively associated with the protruding members 22 and 24 of the screw 12. The first screw is rigidly connected to the second screw by placement of the plate 36 over the protruding members respectively. Openings 42 are provided to accommodate the protruding members 22, 24 by use of two slots disposed at the first end 38 for insertion of the protruding members of the first screw and two slots 44 disposed in the second end 40 for insertion of the protruding members of the sagittal placed second screw. The connecting member 36 is rigidly secured to the screws 12 by use of metal nuts 46 having an internal thread 48 engageable with the threaded surface 34 of each protruding member.

A means for spacing the traverse support member a predetermined distance from the saddle surface 26 is accomplished by use of a washer 50 having an elongated slot for disposition over the protruding members. The screw allowing for placement on a top surface of the alignment support rod 28 placed within the saddle 26. Rod support can also be accomplished by top loading, without a cross link, by use of the screw attachment 12 to the bone with a segmented slotted member 37 to fit directly over the protruding members of the screw. Securement is accomplished by the attachment nuts 46 to the screw 12 causing member 37 to fixate rod 28 in position. This embodiment is preferred for thoraco lumbar stabilization by use of linking the support alignment rods that are placed bilaterally. The use of additional screws, as shown, allow for support along the length of the vertebrae. The metal nuts 46 threaded directly to the top of the screws 12 eliminating the need for movement of muscle during surgery.

Figure 2:
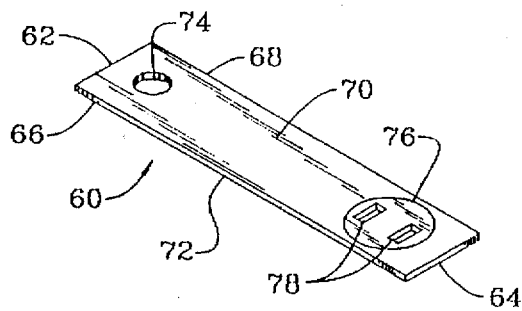
FIG. 2 is perspective view of a variation to the cross-link member support.
Figure 3:
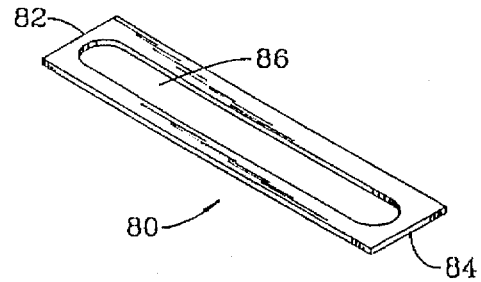
FIG. 3 is perspective view of another variation to the cross-link member support by use of an elongated slot.

Referring in general to FIGS. 2 and 3, a variable angled cross-link sagittal traverse support member is shown having a first end 62 and a second end 64 and two edges 66 & 68 with an upper 70 and a lower 72 reversible surface. The first end 62 includes a centrally disposed opening 74 available for insertion of a cylindrical post commonly used with pedicle screws of the prior art and the variable offset screw of the instant invention described later in this embodiment. At the second end 64 is placed a means for rotating 76 the coupling slots in radial relation to the support member 60. The rotation allowing for the offset of a top loading screw by rotation member 76 permitting placement at variable directions for insertion of the protruding members through the slots 78. Alternatively, a rigid support member 80 can be defined by a first end 82 and a second end 84 with two surfaces therebetween as shown in FIG. 3 wherein an elongated centrally disposed opening or slot 86 extends from the first end to the second end allowing a universally acceptable attachment means for pinon shafts or in the saddle post attachment by use of an enlarged slot.

Figure 4:
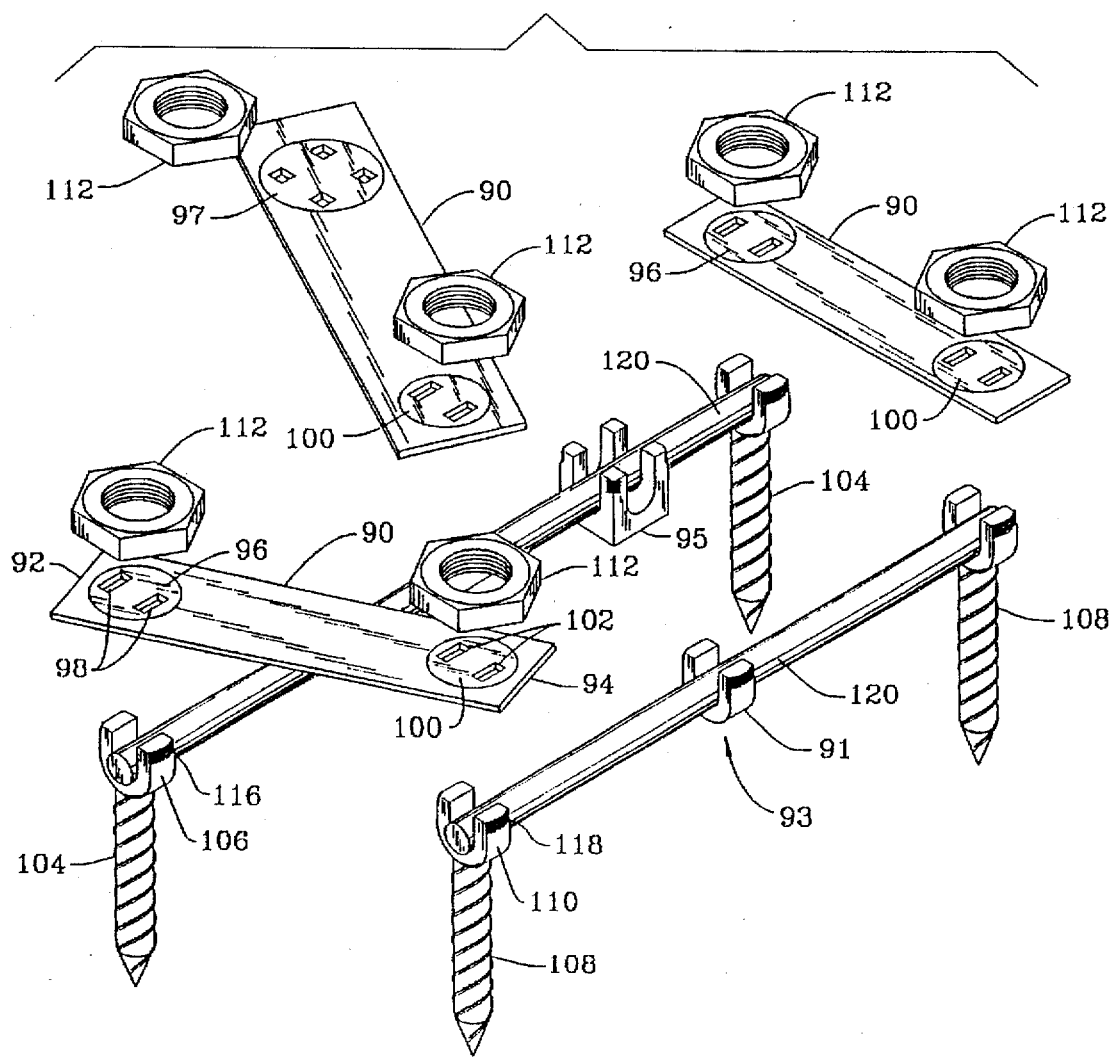
FIG. 4 is a perspective view of the spinal implant using employing the variable cross-link support member.

FIG. 4 illustrates the use of a variable cross-link support member 90 having a first end 92 and a second end 94 with a first rotatable disk 96 for rotating at least two slots 98 in radial relation to the support member 90. A second rotatable disk 100 for rotating at least two slots 102 in radial relation to the support member 90 is disposed at the second end. The disks 96 and 100 are permanently secured to the support member 90 allowing freedom of circular rotation only. The freedom of rotation allows for correction of angle when the screws do not line up directly across the spine. The variable angled support member 90 can be attached to the screw a first screw in the previously described manner by placement of the slots 98 over the protruding members 106 of the saddle end of the screw 104. A second screw 108 can be placed sagittal across the spine but now in a dissimilar plane allowing a surgeon to custom place the screw 108 in the strongest area of the bone eliminating the need to bridge a damaged or degenerative area. The slots 102 are placed over the protruding members 110 of the saddle end of the screw 108. The metal nuts 112 are used for engagement with the outer surfaces 116 and 118 of the corresponding protruding members. The support member 90 residing tightly against the alignment support rod 120 causing a frictional engagement with the inner surface of the saddle. The variable angled support member is made of a variety of lengths for spanning any length range. As shown a second support member 90 is shown is a directly traversing manner wherein the rotatable disks 96 and 100 are placed in a conventional format for placement over the screws 104 and 108. The benefit of the rotatable disk is especially noticeable where the disk may need only a minute movement to accommodate the situation whereas the prior are would require screw removal and replacement.

The system includes the flexibility to attach a cross-link without screw support yet employ the top loading benefit. In this embodiment a U-shaped saddle 91 can be placed about the support rod 120 with a second sagittal placed saddle support 95 shown here in a four protruding member design. Variable crosslink support member 90 with a first rotatable disk 97 for rotating at the four slots in radial relation to the support member 90. A second rotatable disk 100 is placed at the opposite end for rotating at the two slots in radial relation to the support member 90. The freedom of rotation allows for correction of angle when the attachment devices 91 and 95 do not line up directly across the spine. The metal nuts 112 engage the outer surfaces of the corresponding protruding members. The support member 90 residing tightly against the alignment support rod 120 causing a frictional engagement with the inner surface of the saddle.

Figure 5:
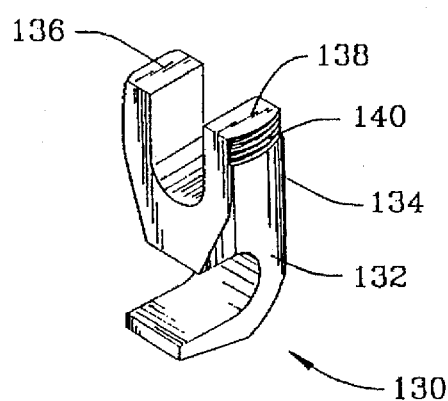
FIG. 5 is a perspective view of the bifurcated externally threaded hook attachment.
Figure 6:
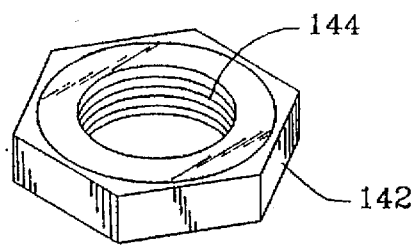
FIG. 6 is a perspective view of the attachment nut for use with the spinal screw of FIG. 5.

FIGS. 5 and 6 illustrate a perspective view of a caudal facing hook 130 having a hook shaped base 132 formed integral with a saddle shaped upper portion 134. The saddle shape portion illustrates the protruding member 136 and 138 common to the invention with the threads 140 cast into the outer surface of the members. The saddle in this type of hook allows for attachment directly onto an alignment support rod wherein the metal nut 142 includes internal threads 144 engageable directly with the hook body 130 threads 140 securely fastening the hook in position. Although not shown, but deemed a part of this invention, is the use of various hook embodiments such as claw and fork hook which employ the top-loading threaded attachment of the instant invention. Unique to this invention is the ability to top-load the screw, attachment device, or hook member allowing the surgeon to perform all couplings from directly above the spine, as compared to the prior art requiring the attachment from the side. The importance of this factor cannot be emphasized enough, or illustrated by drawings, as the amount of muscle that encompasses the spinal area must be moved to accommodate the prior art attachment methods.

Figure 7:
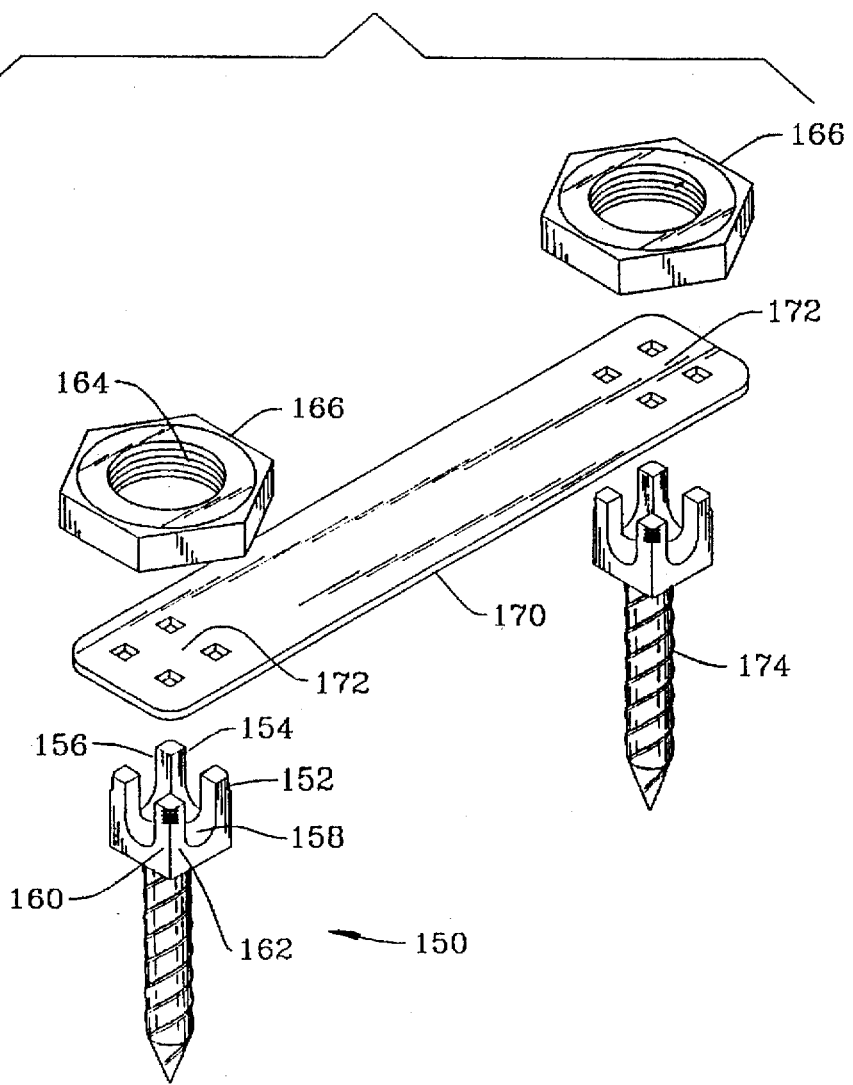
FIG. 7 is an exploded perspective view of a four protruding member spinal screw embodiment.

Now referring to FIG. 7, shown is an alternative embodiment of the screw attachment 150 having four spaced apart protruding members 152. Each protruding member having a first side 154 surface and a second side 156 surface forming an arcuate shaped saddle 158. The third side surface 160 and fourth side surface 162 are threaded for engagement with the inner threaded surface 164 of attachment nut 166. The saddle surface adapted for support of an alignment support rod in a longitudinal or perpendicular mode, the increased saddle surface area providing additional stability for use as a hook or the like attachment. Coupling an alignment support rod to the screw 150 requires the use of a rectangular rigid plate 170 defined by four edges rounded at the corners with two side surfaces with four openings 172 placed therethrough at each end operatively associated with the four spaced apart protruding members of the attachment screw 150. The support member allows for interconnecting to a second sagittal disposed and/or a bilaterally placed screw 174. The support member 170 for the four protruding members may also include a means for rotating the four openings 172 in radial relation to the support member 170 by use of a rotatable disk similar to that shown in FIG. 4 which is permanently secured to the support member 170 allowing freedom of circular rotation. The freedom of rotation allowing for correction of angle when the screws do not line up directly across the spine. Singular attachment plates may also be employed when cross-linking is not desired.

Figure 9:
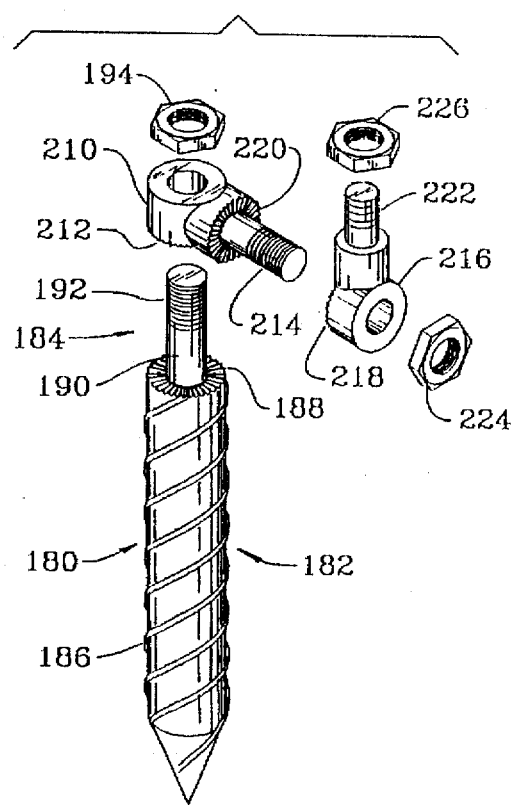
FIG. 9 is an exploded view of a pinion spinal screw with a secondary rotatable direction shaft coupling to the first shaft of FIG. 8.
Figure 8:
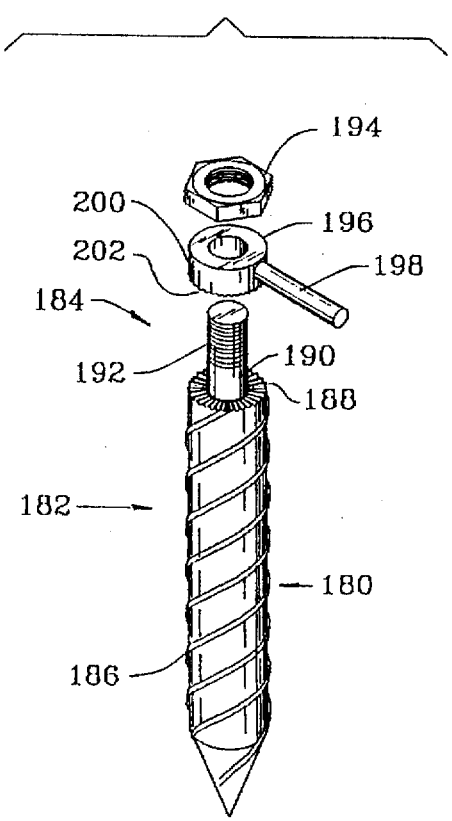
FIG. 8 is an exploded view of a pinion spinal screw with a first rotatable directional shaft.

Referring now to FIGS. 8 and 9, a variable directional attachment screw 180 is shown defined by a first end 182 and a second end 184. The first end 182 having a relatively coarse self-tapping thread 186 over a major portion of its length and a shoulder 188 having a plurality of ridges placed about the circumference. The second end 184 utilizes a rectilinear protruding shaft 190 extending obliquely from the shoulder 188 having a threaded section 192 for use in conjunction with an attachment nut 194. The variable directional screw 182 allows engagement of attachment member 196 having a first directional shaft 198 and base end 200 forming a shoulder. The base end 200 includes a side surface 202 engageable with the shoulder ridges 188 of the screw allowing the base to index about the circumference of the shaft 190 for direction application of the shaft 198. Once a directional locale is depicted, the metal nut 194 is used to engage the threads 192 of the protruding shaft fixing the directional shaft in a stationary position.

As shown in FIG. 9, an alternative base end 210 is shown including a side surface 212 engageable with the shoulder ridges 188 of the screw 182 allowing the base to index about the circumference of the shaft 190 for direction application of a shaft 214. Once a directional locale is depicted, the metal nut 194 is used to engage the threads 192 of the protruding shaft fixing the directional shaft in a stationary position. A second base member 216 can then be added having a side surface 218 engageable with the shoulder ridges 220 located about shaft 214 allowing the second base 216 to index about the circumference of the shaft 214 for direction application of a shaft 222. Once a directional locale is depicted, the metal nut 224 is used to engage the threads of the shaft 214 fixing the directional shaft in a stationary position. A third nut is made available to tightened to devices such as the plates disclosed in FIGS. 2 and 3 for pinion type shaft attachment.

Figure 10:
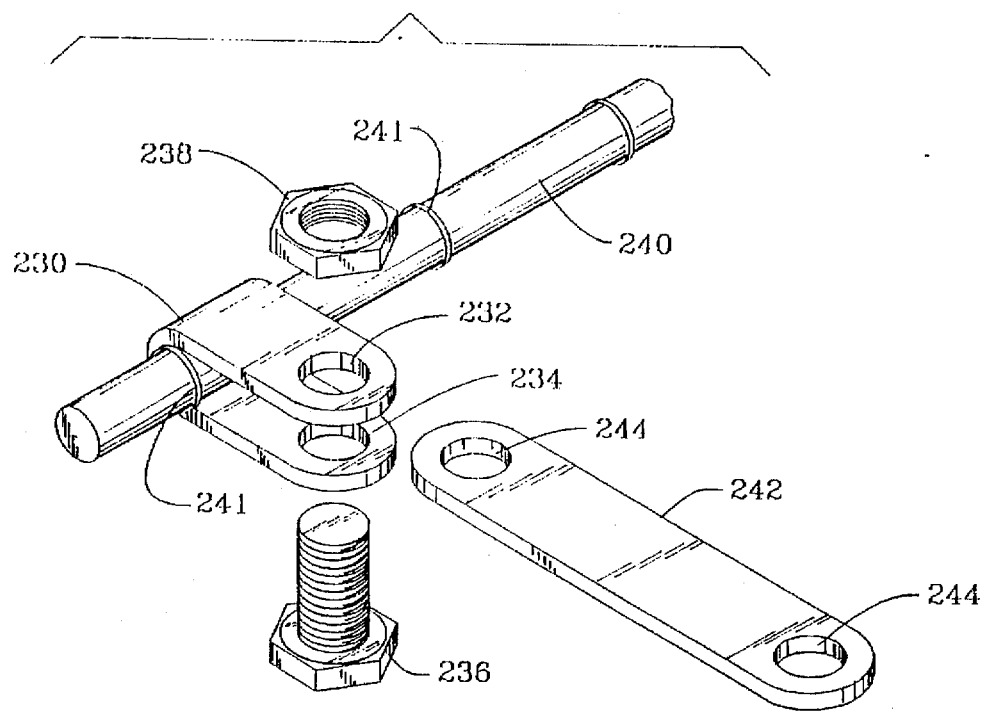
FIG. 10 is an exploded view of a bridge cross-link attachment member employing a C-shaped clamp with bolt and nut.

FIG. 10 illustrates an alternative cross link based upon a C-shaped bracket 230 having two holes 232 and 234 with a peg 236 and nut 238 for locking the bracket 230 in position about a conventional alignment support rod 240. The cross-link 242 can be placed through the pinion type peg 236 by use of attachment holes 244 for stabilizing along the bilateral support rod 240. The cross-link 242 provides stability for a mid-thoracic and is less bulky that the aforementioned cross-links. Further shown is use of an improved alignment rod 240 having a plurality of spaced apart raised ridges 241 to assist in maintaining attachment brackets in a predetermined position.

Figure 11:
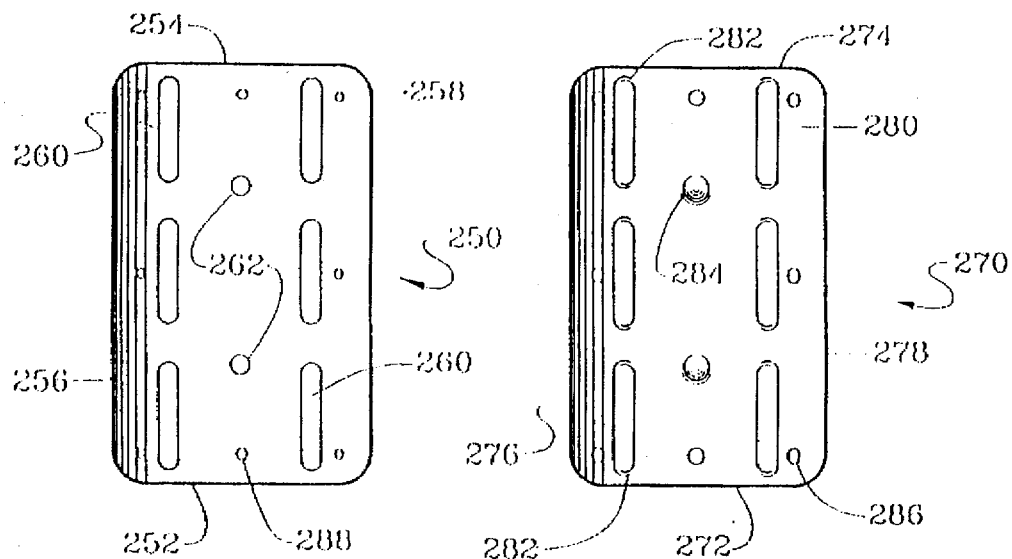
FIG. 11 is a top view of the anterior cervical plates.

FIG. 11 is a anterior cervical plate employing a second plate for locking purposes. Cervical plate 250 is defined as a first rectangular shaped rigid plate having a first end 252 and a second end 254 and two side edges 256 and 258 with a curvature formed between the two edges causing the plate 252 to have a slight curve in it for the cervical curve. The plate utilizes a plurality of openings such as the slots 260 and holes 262 for use in attaching the plate 250 to the cervical by use of conventional bone screws. A second rectangular shaped rigid plate 270 defined by two ends 272 and 274 and two edges 276 and 278 also having a curvature between the two edges is used to couple to the first plate 250 to prevent the bone screws, not shown, from loosening out of the bone. One surface 280 of the place includes a series of indentations 282 and 284 to accommodate the bone screws head. The second plate 270 has a plurality of attachment holes 286 placed about the outer edge of the plate 250 for insertion of threaded screws that which in turn can be threaded in coupling holes 288 placed about the circumference of the first plate 250.

Figure 12:
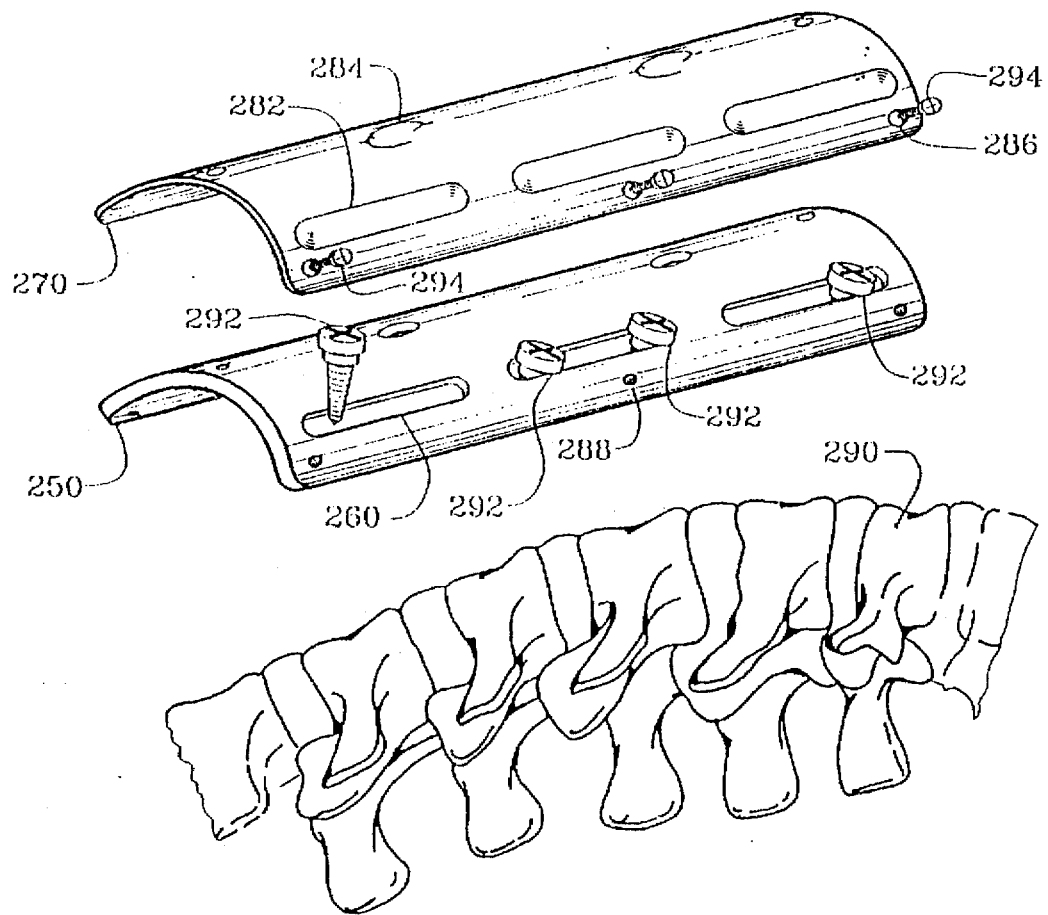
FIG. 12 is a perspective view of the anterior cervical plates available for installation.

As shown in FIG. 12 is a anterior cervical plate employing a second plate for locking purposes. Cervical plate 250 is readily attached to the spine 290 by use of screws 292 placed into the slots 260. The second plate 270 is then placed over the cervical plate 250, the raised indentations 282 and 284 of the plate allowing a flush attachment. Attachment screws 294 are placed through the openings 286 of the second plate and are threaded into threaded openings 288 of the first plate 250. The second plate essentially locking the first plate in position by preventing bone screws 292 from working their way out of the bone.

FIG. 13 is another embodiment of an anterior cervical plate employing a second plate for locking purposes. Cervical plate 300 is defined as a first rectangular shaped rigid plate having a first end 302 and a second end 304 and two side edges 306 and 308 with a curvature formed between the two edges causing the plate 302 to have a slight curve in it for the cervical curve. The plate utilizes a plurality of openings such as the slots 310 and holes 312 for use in attaching the plate 300 to the cervical by use of conventional bone screws. Permanently attached to each side of the plate is attachment strap 314 which includes a means for permanently attaching to strap 316.

A second rectangular shaped rigid plate 320 defined by two ends 322 and 324 and two edges 326 and 328 also having a curvature between the two edges is used to couple to the first plate 300 to prevent the bone screws, not shown, from loosening out of the bone. One surface of the place includes a series of indentations 330 to accommodate the bone screws head. The second plate 320 has two coupling points 332 that are operatively associated with the aforementioned strapping means 314 and 316.

As shown in FIG. 14 the anterior cervical plate is shown attached in a locked position. Cervical plate 30 is readily attached to the spine by use of conventional bone screws placed. The second plate 320 is then placed over the cervical plate 300, the raised indentations of the plate allowing a flush attachment. The attachment straps 314 is then permanently affixed to the second plate 320 followed by attachment straps 316. The attachment straps permanently affixing the two plates in a juxtaposition.

FIG. 15 is still another embodiment of an anterior cervical plate employing a second plate for locking purposes. Cervical plate 350 is defined as a first rectangular shaped rigid plate having a first raised end 352 and a second raised end 354 and two raised side edges 356 and 358 with a curvature formed between the two edges causing the plate 352 to have a slight curve in it for the cervical curve. The plate utilizes a plurality of openings such as the slots 360 for use in attaching the plate 350 to the cervical by use of conventional bone screws. This embodiment employs a plurality of threaded bosses 362 permanently attached to the inner surface of the plate for second plate attachment purposes.

A second rectangular shaped rigid plate 370 defined by two ends 372 and 374 and two edges 376 and 378 also having a curvature between the two edges is used to couple to the first plate 350 to prevent the bone screws, not shown, from loosening out of the bone. The ends and edges fitting within the first plate 350 assimilating a single piece anterior plate. One surface of the second place includes a series of indentations 384 to accommodate the bone screws head used in attaching the first plate to the bone. The second plate 370 having a plurality of holes 380 to accommodate the bosses 362 wherein attachment nuts 382 permanently fasten the two plates in position.

Figure 16:
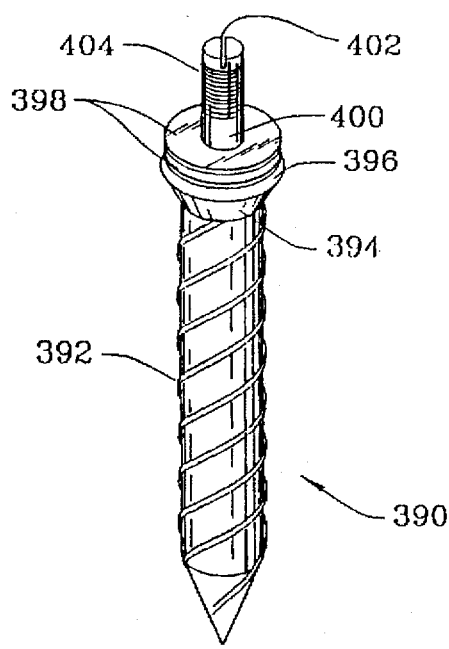
FIG. 16 is an exploded view of a pinion spinal screw with an enlarged shoulder.

Referring now to FIG. 16, a post screw 390 for attachment to the pedicle bone is shown. A first end 392 includes a relatively coarse self-tapping thread over a major portion of its length. A second end 394 forming an enlarged shoulder 396 for bracket support or placement of spacing washers 398. The second end utilizes a rectilinear protruding shaft 400 extending obliquely from the shoulder 396 having a threaded section 404 for Use in conjunction with an attachment nut. Installation can be performed by use of the centrally disposed slot 402 or a hex shaped shaft or shoulder.

Figure 17:
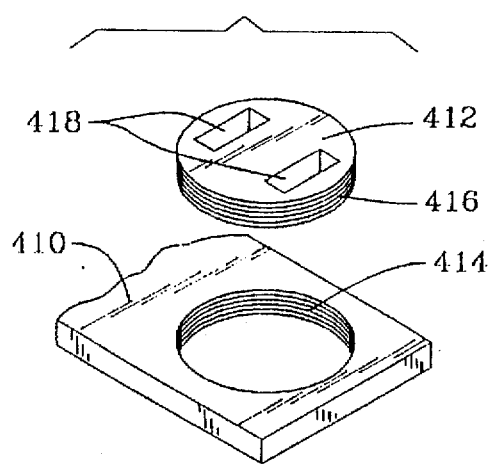
FIG. 17 is a perspective view of a variation to the cross-link member support employing a threaded rotatable member.

Referring to FIG. 17, a variable angled and adjustable cross-link sagittal traverse support member 410 is shown having a finely threaded aperture 414 for insertion of rotatable disk 412 having engagement threads 416. The disk allowing the surgeon to rotate the disk as well as provide a means for vertical adjustment in a manner similarly to the spacing washers.

Figure 18:
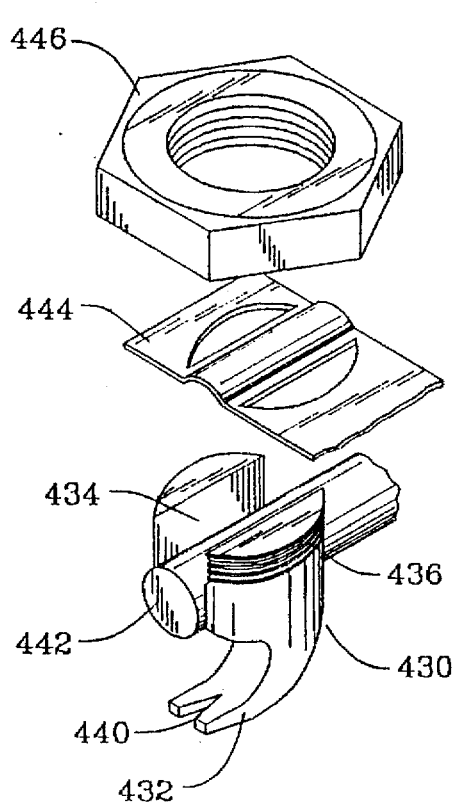
FIG. 18 is a perspective view of an enlarged bifurcated externally threaded hook attachment with a preformed support member.

FIGS. 18 provides a perspective view of an oversized caudal facing hook 430 having a hook shaped base 432 with a fork opening 440 formed integral with a saddle shaped upper portion 434. The saddle shape portion illustrates the enlarged protruding member necessary in instances of large bone attachment or the need of greater strength. The embodiment utilizes a form of four member protrusion with the U-shaped side surfaces thereby providing the additional support. The saddle allows for attachment directly onto an alignment support rod wherein the metal nut 446 includes internal threads engageable directly with the threaded hook body 436. The nut 446 forcing the support plate 444 tightly against the alignment rod 442, the use of a beveled support plate is shown 444 which is preformed to accommodate the curvature of the rod thereby allowing an increase in the surface area of contact.

It is to be understood that while we have illustrated and described certain forms of our invention, it is not to be limited to the specific forms or arrangement of components herein described and shown. It will be apparent to those skilled in the art that various changes may be made without departing from the scope of the invention and the invention is not to be considered limited to what is shown in the drawings and described in the specification.

What is claimed is:

1. A variable directional screw for use in combination with support brackets in a surgical implant for the stabilization of a human spine, said device comprising:

a metal sacral screw base having a first end and a second end, said first end having an insertion tip with a relatively coarse self-tapping thread extending from said insertion tip along substantial portion of said first end, said second end defined as a protruding shaft extending outwardly from said first end with at least a portion of said protruding shaft threaded, said protruding shaft having a diameter less than the diameter of said first end forming a side wall juncture between said first end and second end;

a first directional shaft having a coupling end and an engagement end, said coupling end including an aperture sized for slidable positioning over said protruding shaft of said second end; and at least one nut having internal threads engageable with said threads of said protruding shaft; wherein said first end is insertable into bone and said second end receptive to direct bracket coupling or to the coupling of said directional shaft allowing rotational and perpendicular positioning of said threaded shaft permitting coupling to a bracket at a perpendicular position, said nut locking said directional shaft in a fixed position.

2. The variable directional screw according to claim 1 wherein said side wall includes ridges for frictionally engaging said directional shaft.

3. The variable directional screw according to claim 1 wherein a side surface of said coupling end includes ridges for frictionally engaging said side wall of said first end.

4. The variable directional screw according to claims 2 or 3 wherein said ridges allow said first end and said directional shaft to interdigitate.

5. The variable directional screw according to claim 1 including a second direction shaft having a coupling end including an aperature sized for slidable positioning over said protruding shaft of said first directional shaft and a threaded protruding end with at least one nut having internal threads engageable with said threaded protruding shaft.

6. A variable directional screw for use in combination with support brackets as a surgical implant used in the stabilization of a human spine, said device comprising:

a metal sacral screw base having a first end and a second end, said first end having an insertion tip with a relatively coarse self-tapping thread extending from said insertion tip along a substantial portion of said first end, said second end defined as protruding shaft extending outwardly from said first end with at least a portion of said shaft threaded, said shaft having a diameter less than the diameter of said first end forming a side wall juncture between said first end and second end; said side wall juncture including indexing ridges;

a first directional shaft having a coupling end and an engagement end, said coupling end including an aperture sized for slidable positioning over said shaft of said second end, a side surface of said coupling end including indexing ridges operatively associated with said indexing ridges of said side wall juncture;

and at least one nut having internal threads engageable with said threads of said protruding shaft;

wherein said first end is insertable into bone and said second end can be coupled directly to a bracket or is receptive to the coupling of said directional shaft allowing 360 degree rotation and perpendicular positioning of said threaded shaft with said ridges allowing said base and said directional shaft to interdigitate, said nut locking said directional shaft in a fixed position.

7. The variable directional screw according to claim 6 including a second direction shaft having a first end formed of a shoulder having a side surface engageable with the ridges of said first directional shaft, said shaft protruding perpendicular therefrom with at least one metal nut having internal threads engageable with said threaded protruding shaft.

* * * * *